(12) United States Patent
Iannotti (10) Patent No.: US 12,303,213 B2
(45) Date of Patent: May 20, 2025

(54) PREOPERATIVE IMAGING COMBINED WITH INTRAOPERATIVE NAVIGATION BEFORE AND AFTER REMOVAL OF AN IMPLANT FROM A SURGICAL SITE TO CREATE A COMPOSITE SURGICAL THREE DIMENSIONAL STRUCTURAL DATASET

(71) Applicant: JPI Consulting, Delray Beach, FL (US)

(72) Inventor: Joseph P. Iannotti, Delray Beach, FL (US)

(73) Assignee: JPI Consulting, Delray Beach, FL (US)

( * ) Notice: Subject to any disclaimer, the term of this patent is extended or adjusted under 35 U.S.C. 154(b) by 0 days.

(21) Appl. No.: 18/195,655

(22) Filed: May 10, 2023

(65) Prior Publication Data

US 2024/0024035 A1    Jan. 25, 2024

Related U.S. Application Data

(60) Provisional application No. 63/391,103, filed on Jul. 21, 2022.

(51) Int. Cl.
*A61B 34/20* (2016.01)
*G06T 7/30* (2017.01)

(52) U.S. Cl.
CPC .............. *A61B 34/20* (2016.02); *G06T 7/30* (2017.01); *A61B 2034/2065* (2016.02); *G06T 2207/10081* (2013.01); *G06T 2207/20221* (2013.01); *G06T 2207/30008* (2013.01); *G06T 2207/30052* (2013.01)

(58) Field of Classification Search
CPC ............ A61B 34/20; A61B 2034/2065; A61B 2034/102; A61B 2034/105; A61B 34/10; G06T 7/30; G06T 2207/10081; G06T 2207/20221; G06T 2207/30008; G06T 2207/30052
See application file for complete search history.

(56) References Cited

U.S. PATENT DOCUMENTS

| | | | |
|---|---|---|---|
| 5,484,446 A | 1/1996 | Burke |
| 6,712,824 B2 | 3/2004 | Millard |
| 7,658,741 B2 | 2/2010 | Claypool |
| 7,744,600 B2 | 6/2010 | Rangaiah |
| 8,236,000 B2 | 8/2012 | Ammann |

(Continued)

FOREIGN PATENT DOCUMENTS

| | | |
|---|---|---|
| WO | 2017/204832 A1 | 11/2017 |
| WO | 2018/013848 A1 | 1/2018 |
| WO | 2020/216934 | 10/2020 |

OTHER PUBLICATIONS

ISA/US International Search Report for International Application No. PCT/US23/27969, filed Jul. 18, 2023 (4 pages).

(Continued)

*Primary Examiner* — Bo Joseph Peng
(74) *Attorney, Agent, or Firm* — Rowan Tree Law Group, PLLC; Joseph W. Schmidt (57) ABSTRACT

A method comprises combining one or more pre-operative data sets of an anatomical site in an unaltered condition and one or more intraoperative data sets of the anatomical site in an altered condition to form one or more composite data sets of the anatomical site and using the one or more composite data sets to assist in navigation within the anatomical site in association with one or more surgical processes.

17 Claims, 12 Drawing Sheets

(56) References Cited

U.S. PATENT DOCUMENTS

| | | |
|---|---|---|
| 8,403,934 B2 | 3/2013 | Angibaud |
| 9,386,998 B2 | 7/2016 | Wilkinson |
| 10,002,227 B2 | 6/2018 | Netravali |
| 10,940,021 B2 | 3/2021 | Mahfouz |
| 11,007,012 B2 | 5/2021 | Netravali |
| 11,026,700 B2 | 6/2021 | Shah |
| 2007/0100258 A1 | 5/2007 | Shoham |
| 2017/0004832 A1 | 1/2017 | Du et al. |
| 2017/0189131 A1 | 7/2017 | Weir |
| 2017/0258526 A1* | 9/2017 | Lang .................. A61B 34/10 |
| 2019/0015167 A1 | 1/2019 | Draelos |
| 2019/0069961 A1 | 3/2019 | Smith |
| 2020/0093502 A1 | 3/2020 | Jones |
| 2022/0296302 A1 | 9/2022 | Bleunven |

OTHER PUBLICATIONS

ISA/US International Written Opinion for International Application No. PCT/US23/27969, filed Jul. 18, 2023 (4 pages).
ISA/US International Search Report for corresponding International Application No. PCT/US23/20951, filed May 4, 2023 (10 pages).
ISA/US International Written Opinion for corresponding International Application No. PCT/US23/20951, filed May 4, 2023 (2 pages).

* cited by examiner

"SRI"

PREOPERATIVE IMAGING COMBINED WITH INTRAOPERATIVE NAVIGATION BEFORE AND AFTER REMOVAL OF AN IMPLANT FROM A SURGICAL SITE TO CREATE A COMPOSITE SURGICAL THREE DIMENSIONAL STRUCTURAL DATASET

CROSS-REFERENCE TO RELATED APPLICATION(S)

The present application claims priority to, and the benefit of, U.S. Provisional Application Serial No. 63/391,103, filed Jul. 21, 2022, the entire contents of which are incorporated by reference herein.

BACKGROUND

The present invention is directed to a method and system for generating composite three dimensional (3D) structural datasets of a surgical field that includes 3D structural data of the surgical field obtained preoperatively and structural 3D data of the altered surgical field obtained intraoperatively. In this composite 3D dataset, a surgical reference instrument is incorporated into both the intraoperative datasets before and after alternation of the surgical field to assist and guide the surgeon through the surgical procedure. The 3D dataset can be represented as a 3D image that can be manipulated within a software platform.

SUMMARY

The present invention has application, for example, in revision surgery, in association with orthopedic joint, trauma, maxillofacial, dental, shoulder, hip, cranial and/or spinal surgery. The present invention has particular application where an implant, for example, a metal implant produces erroneous data (due to the presence, e.g., of a metal artifact), on a preoperative image within the region of the intended reconstructive surgery and therefore distorts the image. This commonly occurs, for example, with computed tomographic and magnetic resonance imaging. More specifically, when these images are obtained in association with preoperative imaging for revision surgery, accurate assessment of the surrounding anatomy is difficult and compromised due at least in part to the presence of a metal implant artifact. The distorted image data makes preoperative surgical planning, implant selection and implant placement at the time of surgery difficult and inaccurate, and negatively affects the utilization of currently available patient specific instrument or intraoperative navigation technologies. Although some current practices utilize metal artifact reduction technologies which address some of the imaging concerns, issues still arise and they are not fully effective, i.e., the current artifact reduction problems do not eliminate all of the problems associated with preoperative imaging and surgical planning. In addition, current practices are incapable of predicting and/or generating the final 3D surgical anatomy after removal of the implant because they cannot predict the anatomy that will remain after removal of the implant and are also incapable of providing adequate guidance for reconstruction or placement of a new implant.

In accordance with illustrative embodiments, the present invention is directed to the combined use of available preoperative metal artifact reduction image acquisition and post image processing technology with intraoperative digitization (mapping) of the surgical anatomy both prior to removal of the implant and after removal of the implant, and preparation of the surgical site to create a composite 3D surgical structural dataset (optionally generated as an image) that combines the newly created surface architecture created by removal of the implant with the unaltered structural anatomy obtained from the preoperative imaging not altered by the metal artifact. In illustrative embodiments, the innovation also includes the placement of a reference instrument within the surgical site prior to removal of the implant in an area not to be altered during the surgery. The reference instrument is registered with the composite 3D structural dataset (with optional generated image) both before and after removal of the implant, and is used to assist the surgeon in performing the final surgical reconstruction. More specifically, the reference instrument is used after removal of the implant from within the composite structural dataset (optional generated image) to assist the surgeon using computer aided and or robotically controlled surgical instrumentation to prepare the surgical site, select and place the new implant using existing surgical navigation techniques which may be augmented relative to the use of an adjustable patient specific instrumentation.

One illustrative embodiment would be in revision shoulder arthroplasty where the glenoid component is removed and replaced with another implant. In this application, preoperative metal artifact reduction 3D CT imaging is performed to determine the status of the implant and estimate of the amount of glenoid bone remaining for reconstruction after removal of the implant. These images are limited by both the metal artifact and the inability to reliably predict the amount of glenoid bone that will remain after removal of the implant and other material such as fibrous tissue, bone cement or poor-quality bone.

The complex 3D anatomy of the remaining glenoid cavity is not known until this portion of the surgery is completed. In the reconstruction and placement of a new implant, bone grafts, metal augments and screws are placed into the glenoid cavity, their location and orientation are placed in relation to the scapula and scapula bone columns that are seen on the preoperative imaging but not seen at the time of surgery. Knowing the 3D relationship of the remaining glenoid cavity in the surgery after removal of the implant in relation to the remaining scapula anatomy that is not altered by the surgery and seen on the preoperative imaging are often critical to getting fixation of the new implant. Also, some of the unaltered scapula structures that are seen in the preoperative 3D dataset are not seen at the time of surgery because they are not in the surgical field. The relationship of these anatomic structures to the new 3D anatomy of the glenoid created at the time of surgery after removal of the implant and other material need to be linked into a composite 3D dataset to assist in surgical reconstruction. Creating the 3D composite structural dataset may be further assisted by use of a reference instrument that is contained within that composite and that instrument can assist in active navigation of the placement of the new implant and its component parts and screw fixation to portions of the scapula on seen on the composite 3D dataset.

BRIEF DESCRIPTION OF THE DRAWINGS

Various aspects and features of the present disclosure are described hereinbelow with references to the drawings, wherein.

DETAILED DESCRIPTION

Particular embodiments of the present disclosure are described hereinbelow with reference to the accompanying drawings. However, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

The present disclosure has application across many technologies, including, but not limited to, various types of orthopedic procedures such as shoulder, knee, hip and ankle repair or any other arthroplasty surgical procedure. The present disclosure also has application in dental, spinal or cranial surgical procedures.

Generally stated, the present invention is directed to a system and methodology for combining intraoperative three (3D) data set before and after alteration of the anatomy with preoperative (3D dataset) imaging to create a series of composite 3D datasets (represented as images) of the surgical field to assist the surgeon in performing one or more surgical procedures. The datasets can be represented as a 3D image that can me manipulated in the software platform but one or more of these composite images are not required in the performance of this procedure.

Figure 1:
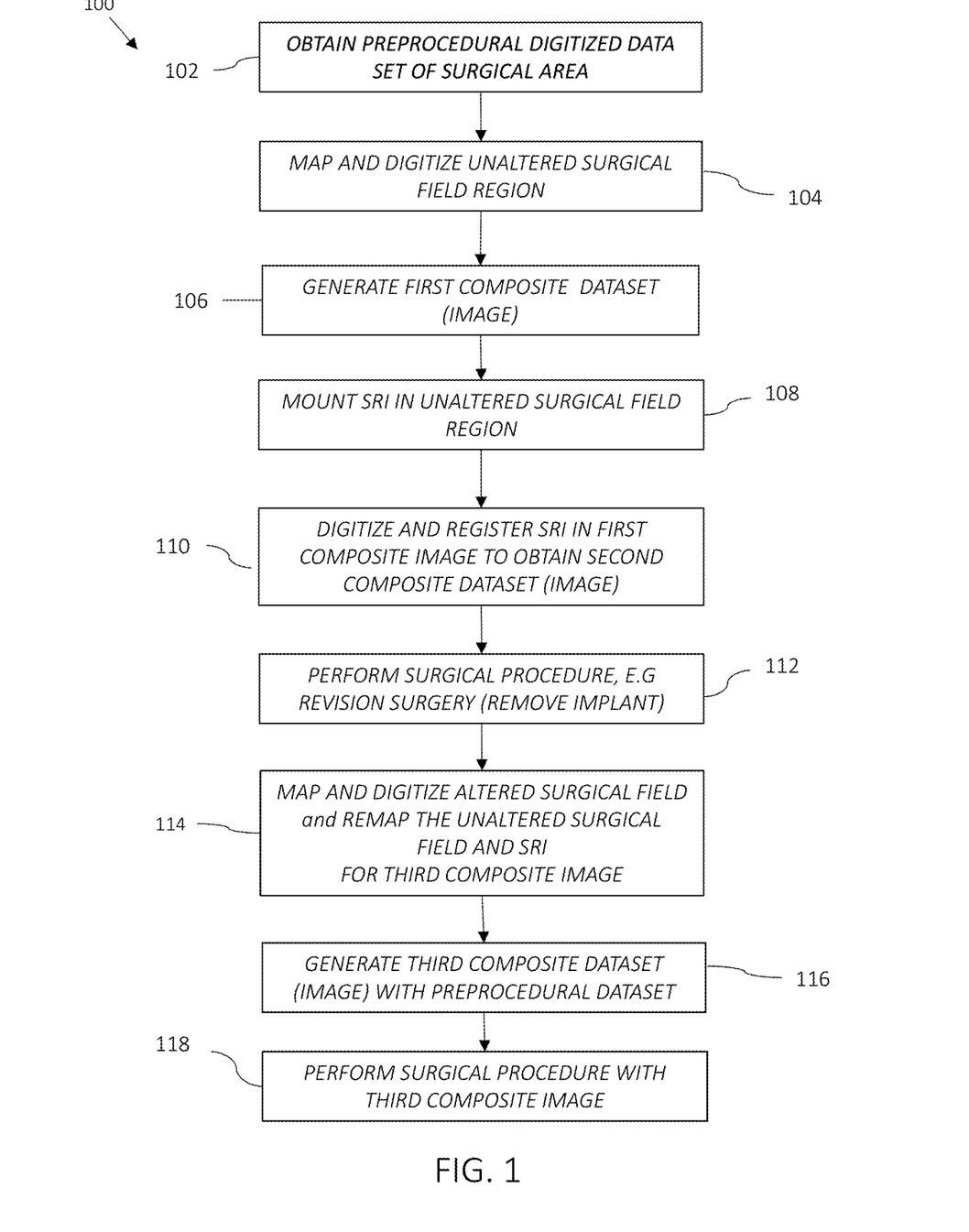
FIG. 1 is a flow chart illustrating a method of using the system in accordance with one or more exemplative embodiments of the present disclosure.
Figure 2A:
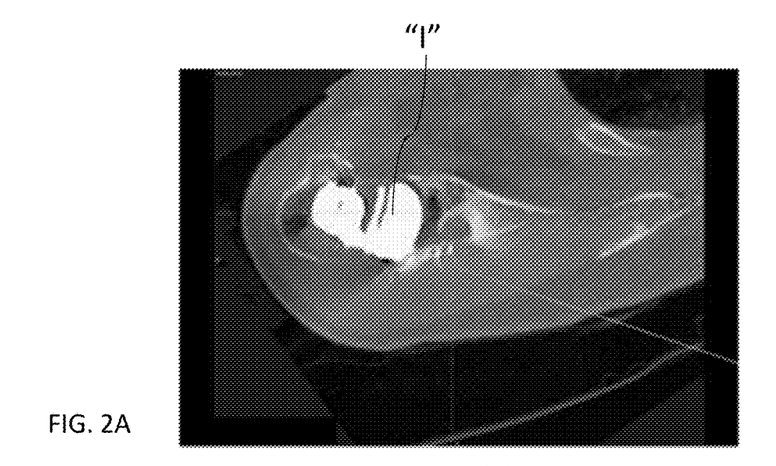
FIGS. 2A-2D are 2-dimensional (2D) and 3-dimensional (3D) views of the 3D dataset of the scapula area of a subject with a metal implant obtained via x-ray tomographic imaging in association with a preoperative phase of a surgical procedure to enable generation of a preoperative plan in accordance with one or more exemplative embodiments of the present disclosure.
Figure 2B:
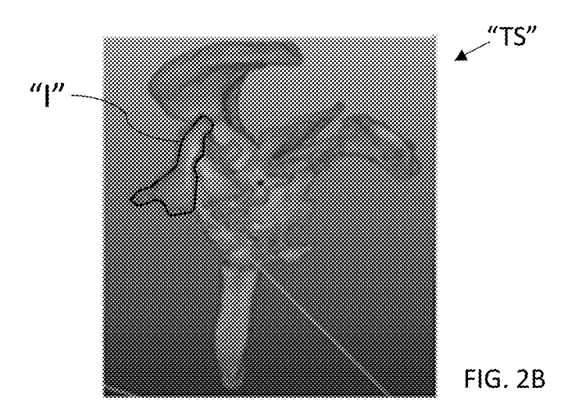
Figure 2C:
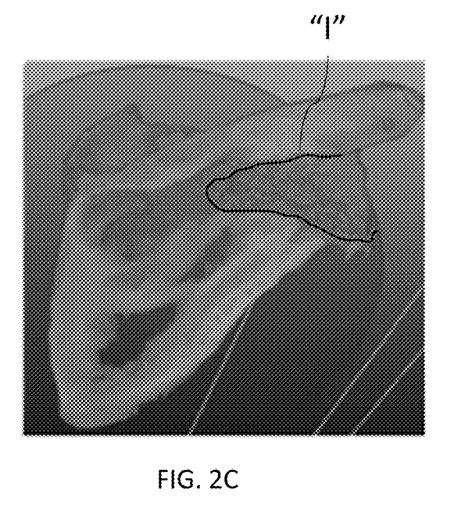
Figure 2D:
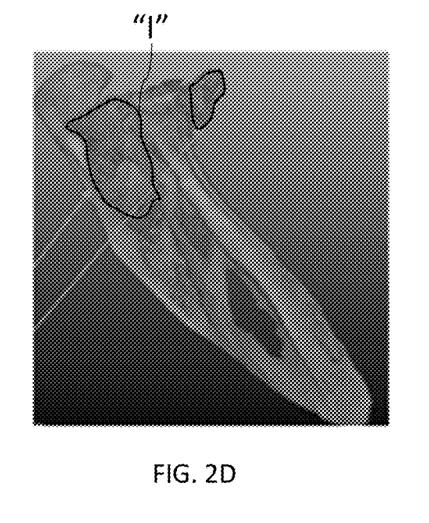
Figure 3A:
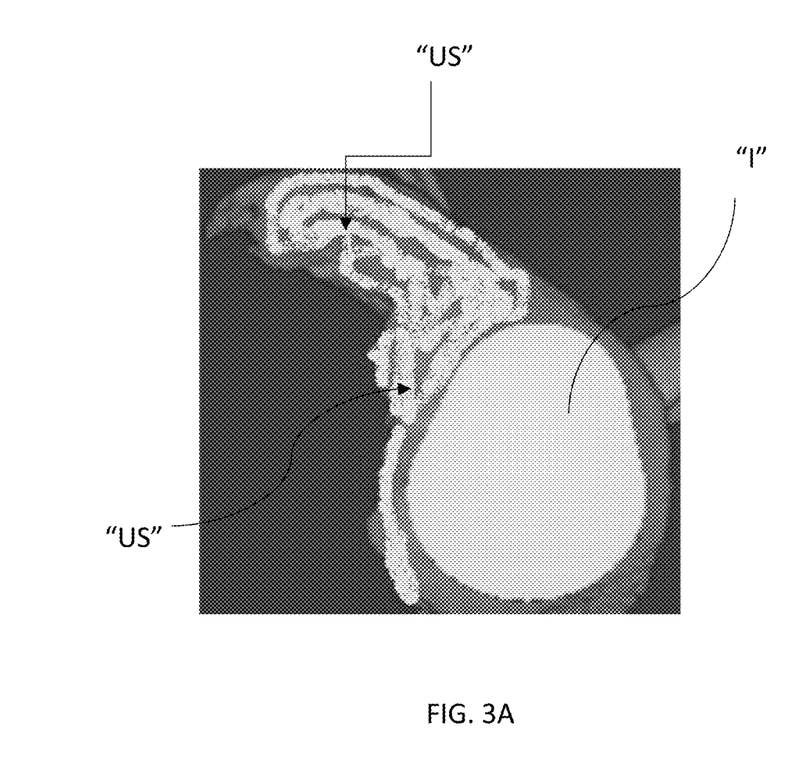
FIGS. 3A and 3B are images of the 3D dataset of the glenoid bone of the scapula area and a glenoid implant illustrating portions of the glenoid bone and coracoid process surrounding the glenoid implant which is subject to intraoperative digitization to create a 3D dataset to be registered to the preoperative 3D dataset prior to removal of the implant in accordance with one or more exemplative embodiments of the present disclosure.
Figure 3B:
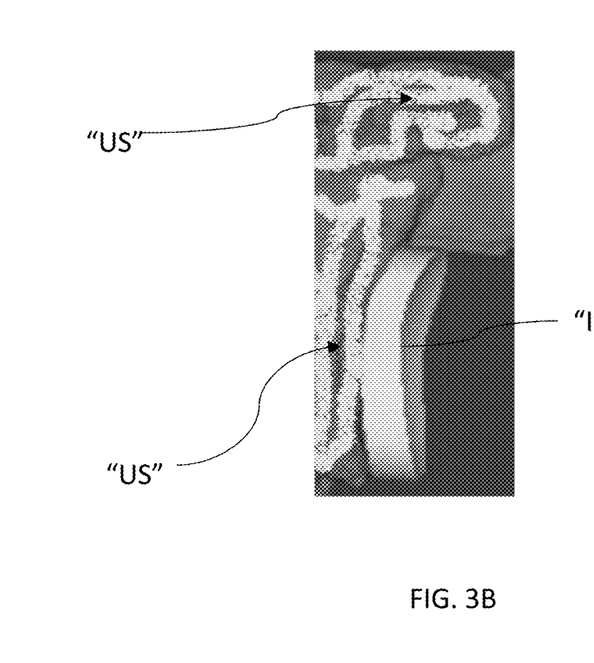
Figure 4:
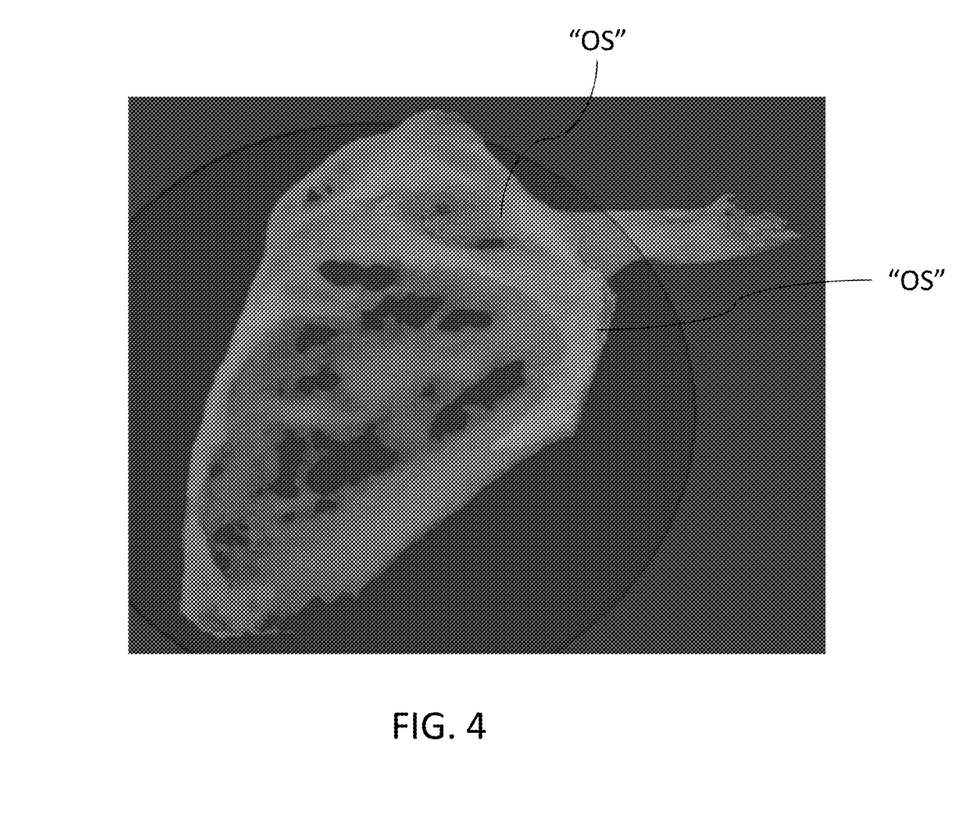
FIG. 4 is a view illustrating a portion of the 3D dataset of the scapula including the coronal plane not visible within the surgical field or subject to digitization and registration with the preoperative imaging (3D dataset) prior to removal of the implant in accordance with one or more exemplative embodiments of the present disclosure.
Figure 7A:
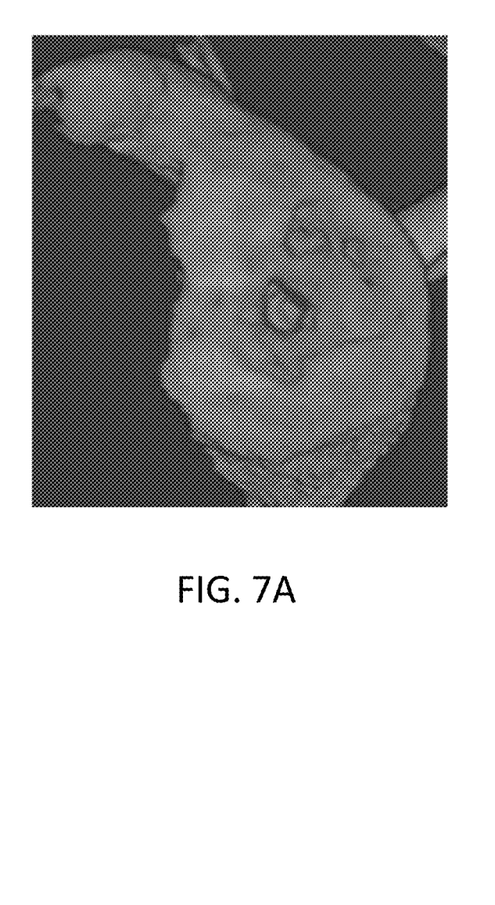
FIG. 7A is a view illustrating removal of the implant in accordance with one or more illustrative embodiments of the present disclosure.
Figure 7B:
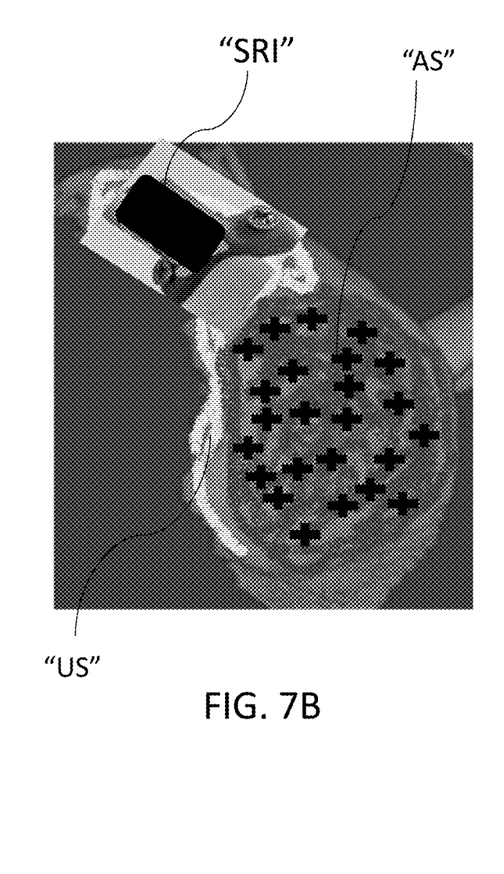
FIGS. 7B and 7C are images of the 3D dataset schematically illustrating mapping and digitization of the surgical reference instrument and the new bone surfaces formed by the removed implant in accordance with one or more illustrative embodiments of the present disclosure.
Figure 7C:
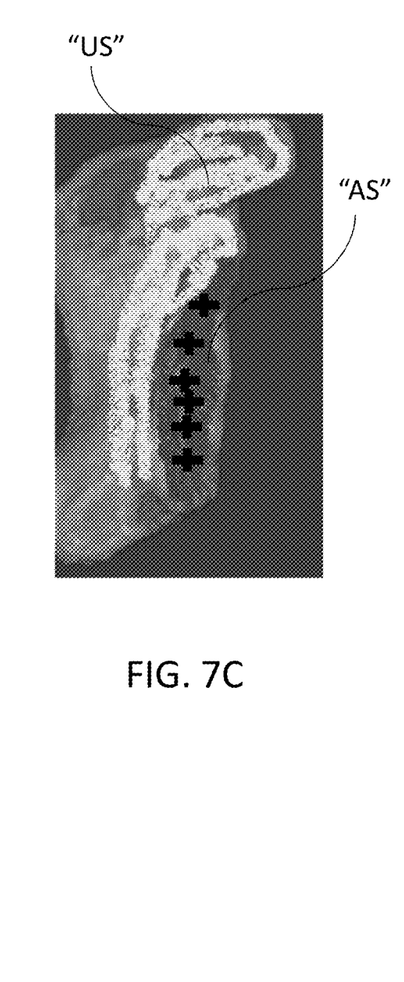
Figure 8A:
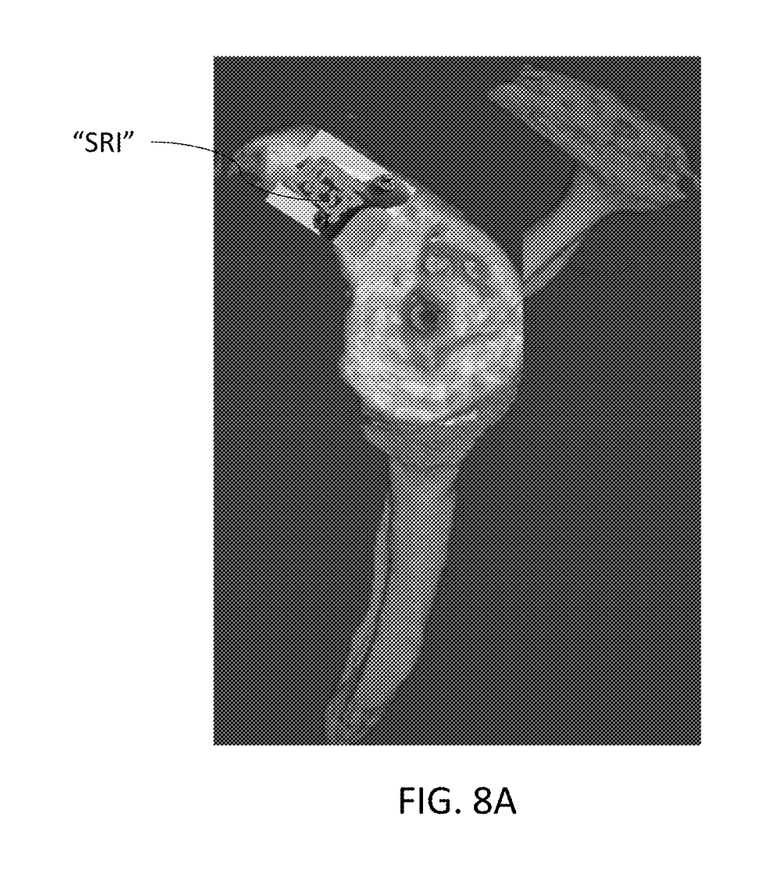
FIGS. 8A and 8B are views illustrating representing registration of the new 3D structural data of the new bone surfaces after removal of the implant with the second composite image containing the preoperative and intraoperative data before implant removal to generate a third composite image in accordance with one or more illustrative embodiments of the present disclosure.
Figure 8B:
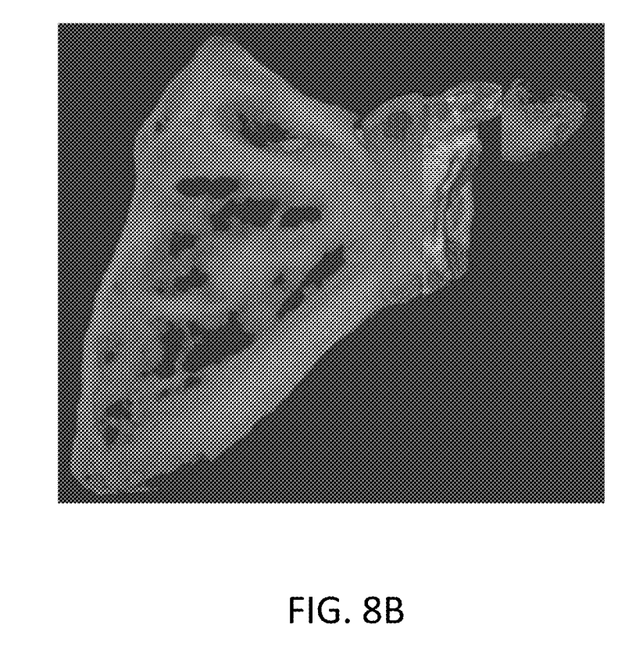
Figure 9A:
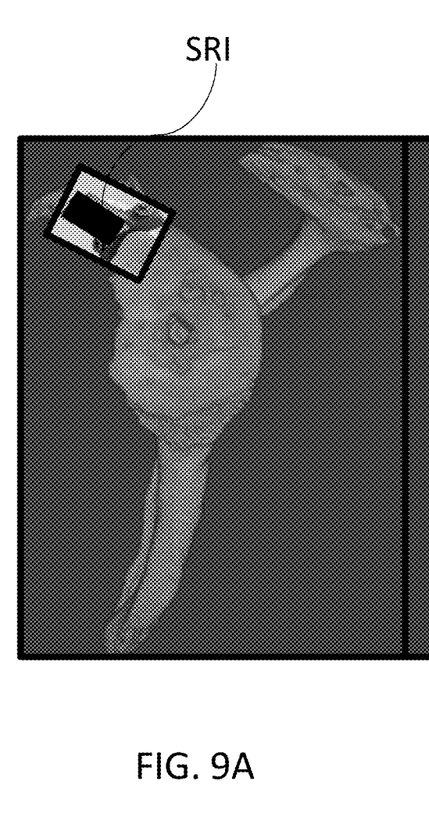
FIGS. 9A-9E are 3D dataset images illustrating use of the third composite image including the altered surgical field with the pre-procedural dataset not defined within the surgical field to define, by intraoperative surgical navigation methods, the location of the new implant and screws in the bone columns of the scapula.
Figure 9B:
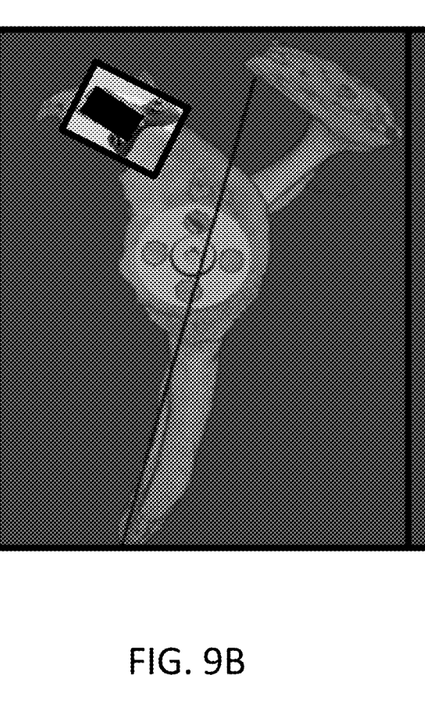
Figure 9C:
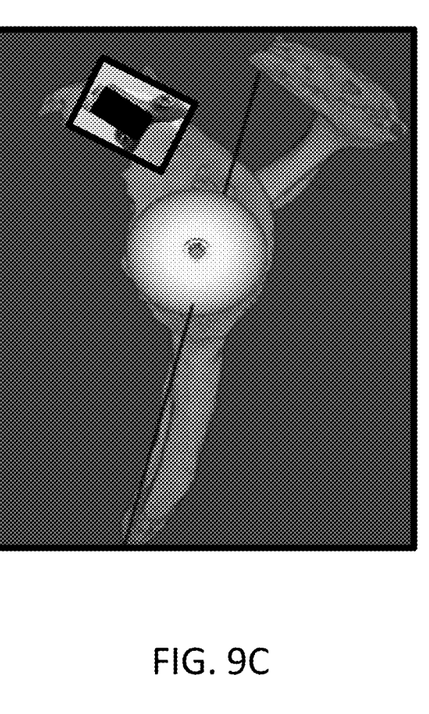
Figure 9D:
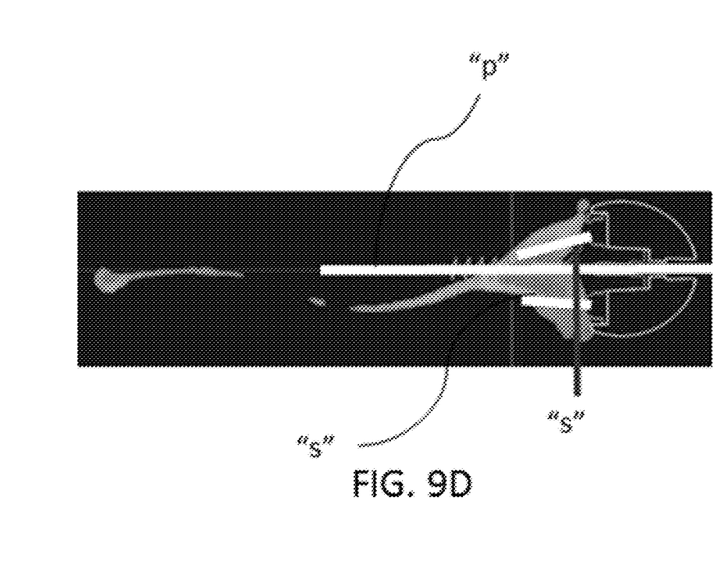
Figure 9E:
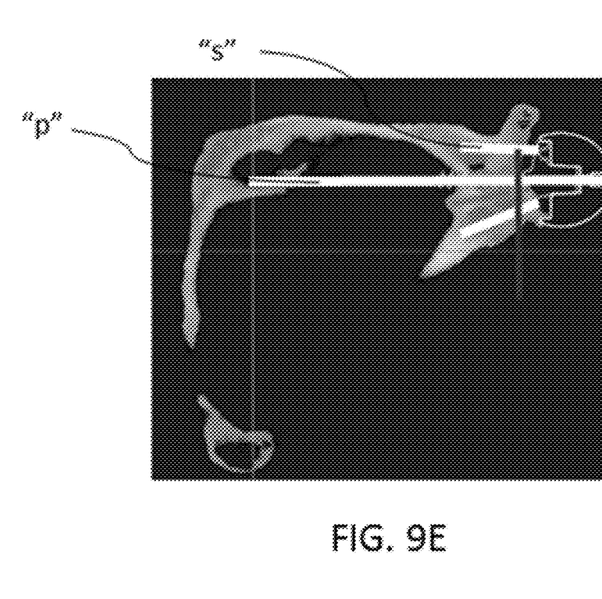
Figures 10A, 10B:
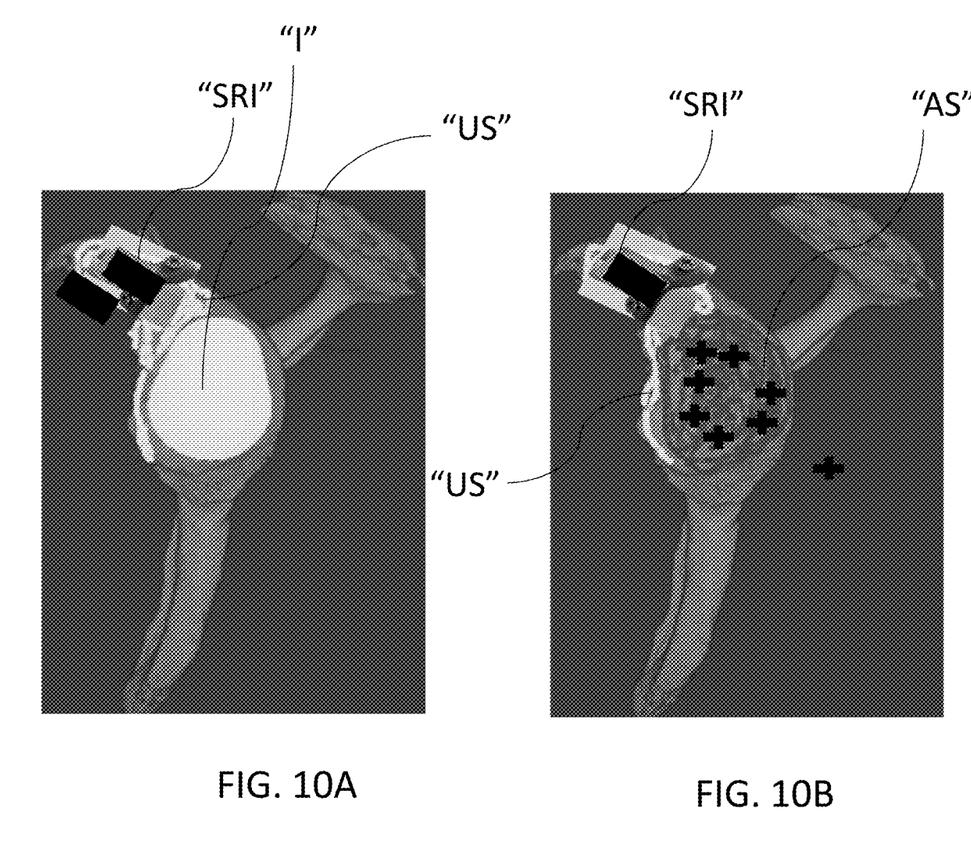
FIGS. 10A-10G is a summary of steps to digitize (map) the glenoid bone before removal of the implant "I" and registration to the scapula with the surgical reference instrument "SRI" (bone mount) (left panel CI-2) with the combined image after removal of the implant and use of remote robotic and PSI technology to intra-operative execution of the surgical plan created at the time of surgery using the third composite image (CI-3) dataset.
Figure 10C:
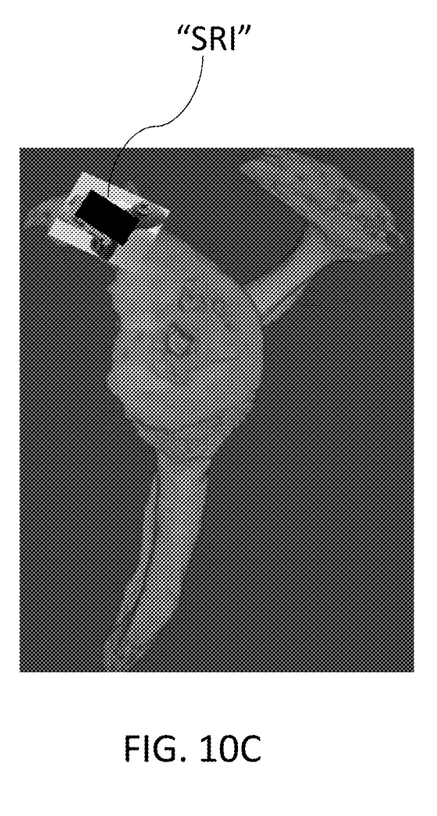
Figure 10D:
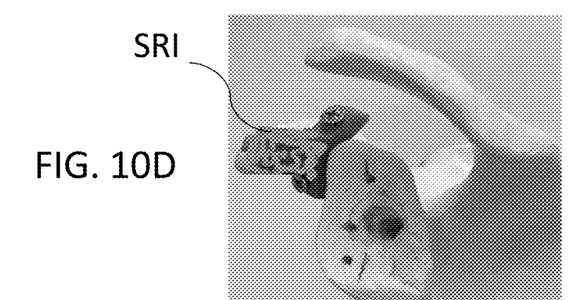
Figure 10E:
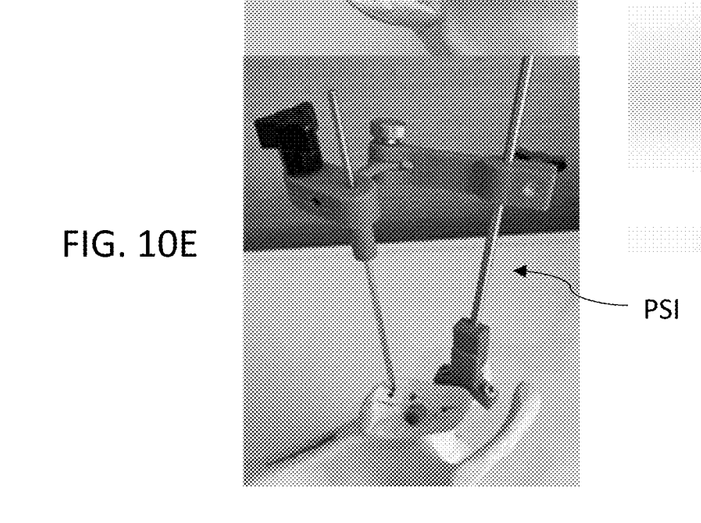
Figure 10F:
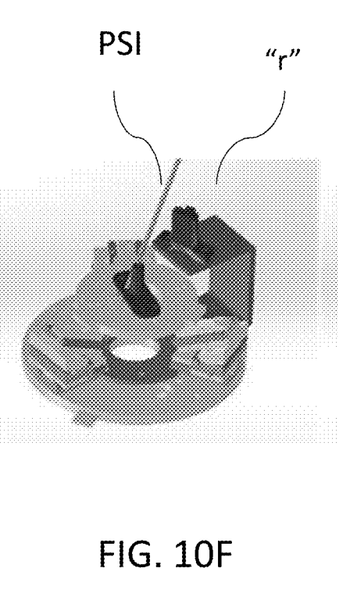
Figure 10G:
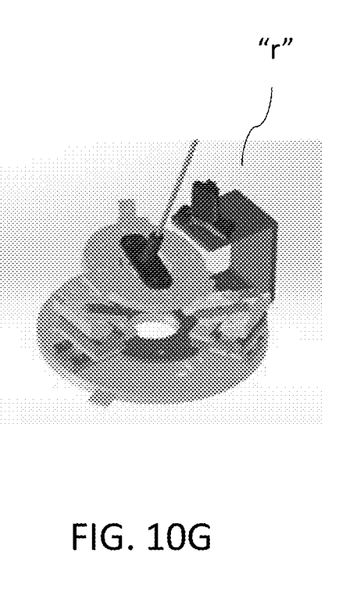

With reference to the flowchart depicted in FIG. 1, one illustrative embodiment of the present invention incorporates at least some of the following steps or processes. In STEP 102 of the flow chart 100, a three-dimensional (3D) preoperative dataset information is obtained through any number of conventional 3D imaging techniques of a surgical field or area of interest, for example, the scapula area. In illustrative embodiments, the preprocedural data set is obtained using, magnetic, ultrasound, x-ray or any method of imaging that defines the 3D shape of an object at the object site. However, it is noted that the preoperative 3D dataset includes the existing implant (for example, a metallic implant) which distorts the dataset as discussed hereinabove. In addition, the resulting structure after removal of the implant cannot be defined with accuracy before it is removed. For example, and without limitation, a preoperative CT scan of the shoulder will provide a 3D dataset of the entire shoulder blade "TS" and the implant as shown in FIGS. 2A-2D including all the structure or bones that are of interest for the surgery. The outline of the implant "I" is visible in FIGS. 2B-2D. Within the preoperative 3D dataset there are structures that will be within the surgical field (FIGS. 3A and 3B) including the implant "I" and anatomy (3D data) of the same bone or other bones that will not be within the surgical field (FIG. 4). Some of these structures can be defined without distortion by metal artifact. The entire 3D dataset of the structure of interest, in the example described the scapula, is the total structure designated hereafter as TS (FIGS. 2A-2D). The structures (parts) of TS within the surgical field can be defined as those being either altered by removal of the implant and others that will not be altered. Hereafter, those structures that are not to be altered are schematically designated as squiggly or randomly curved lines "US" (FIGS. 3A and 3B) and those structures that are altered are schematically designated also as squiggly or randomly curved lines with "+" hashing "AS" (FIGS. 7B and 7C"). The remaining other structures "OS" (FIG. 4) that are in the preoperative (3D Dataset) image TS (shown in CI 1,2,3) that are not altered and not seen within the surgical field but remain important for execution of the surgery before and after removal of the implant.

For example, a revision surgery for a shoulder surgery has an existing implant (which is to be replaced) which compromises or distorts the obtained preoperative dataset that will be within the surgical field. That distortion compromises the ability to define the surgical anatomy of interest. In addition, the surgeon cannot accurately predict of the amount of bone structure which will be left in the shoulder socket upon the subsequent removal of the implant.

Figure 5A:
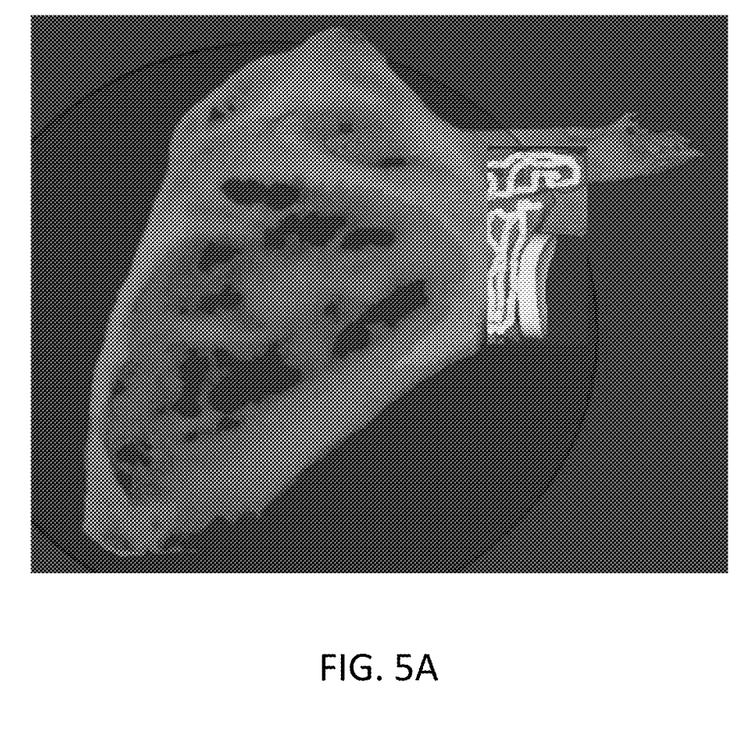
FIGS. 5A and 5B are views illustrating generation of the first composite 3D dataset shown as an image in the coronal and sagittal plane respectively incorporating the anatomy that was digitized in FIGS. 3A and 3B with the preoperative 3D dataset shown as a composite image of FIGS. 2A-2D in accordance with one or more exemplative embodiments of the present disclosure.
Figure 5B:
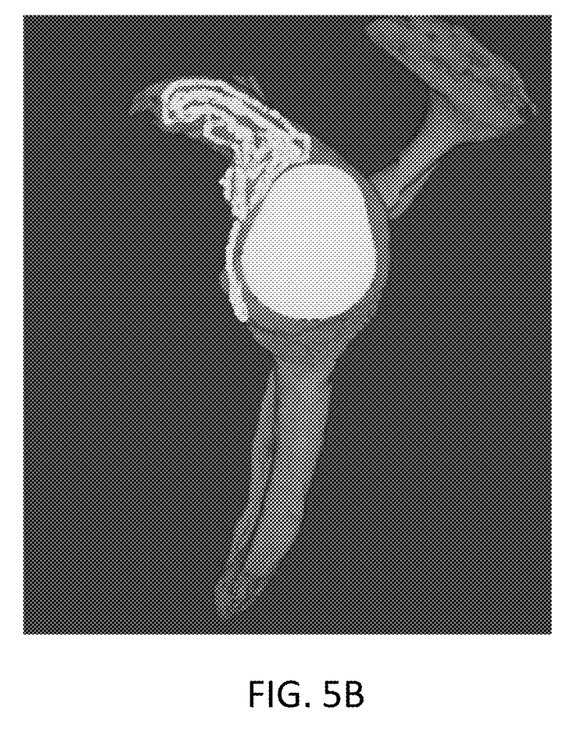

In STEP 104, at the time of surgery, the surgical anatomy is exposed, in this case, the glenoid bone, coracoid and implant. The area of the surgical anatomy which will not be altered "US" during the surgical procedure is identified and digitized using any number of techniques using a contact digital probe with or without optical trackers, laser or optical scanning, stereotactic image capture (FIGS. 3A and 3B). In this example the area digitized (mapped) is the anterior glenoid wall, base of the coracoid and coracoid process. The digitized area "US" is then registered with the preoperative surfaces that correspond to the pre-operative 3D dataset of the same bone using software registration commonly used in surgical navigation techniques. At STEP 106, this generates a first composite image (CI-1) (FIGS. 5A and 5B). The first composite image CS-1 defines a 3D dataset, for example, a first composite 3D dataset, of what is seen in the surgical field with the 3D dataset of the total pre-operative dataset TS.

Figure 6A:
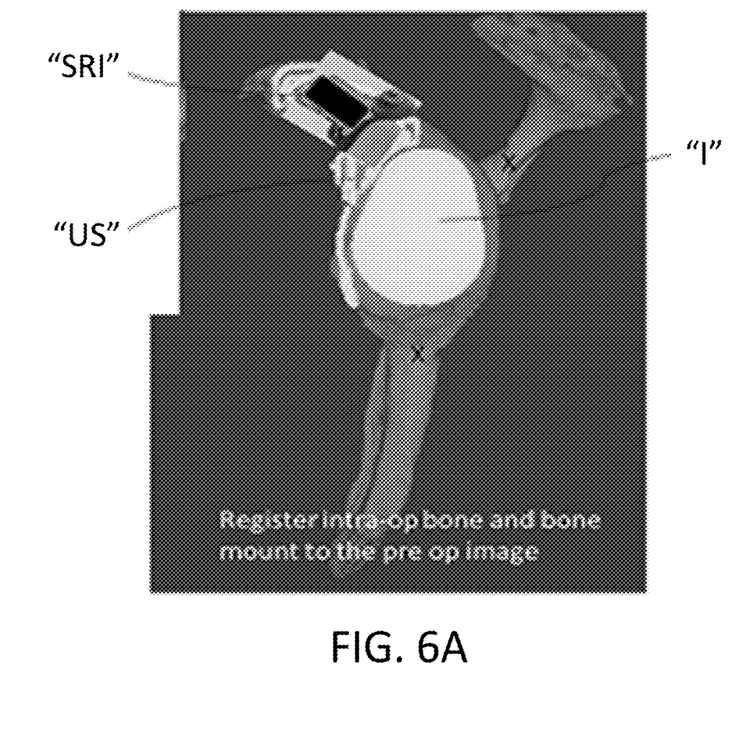
FIGS. 6A and 6B are views illustrating positioning of a surgical reference instrument (SRI) at the base of the coracoid which is digitized and then registered to form a second composite 3D dataset represented as an image that is portion of the bone within the surgical field, before implant removal, and that portion of the bone (scapula) not seen in the surgical field but seen in the pre-procedural 3D dataset in accordance with one or more exemplative embodiments of the present disclosure.
Figure 6B:
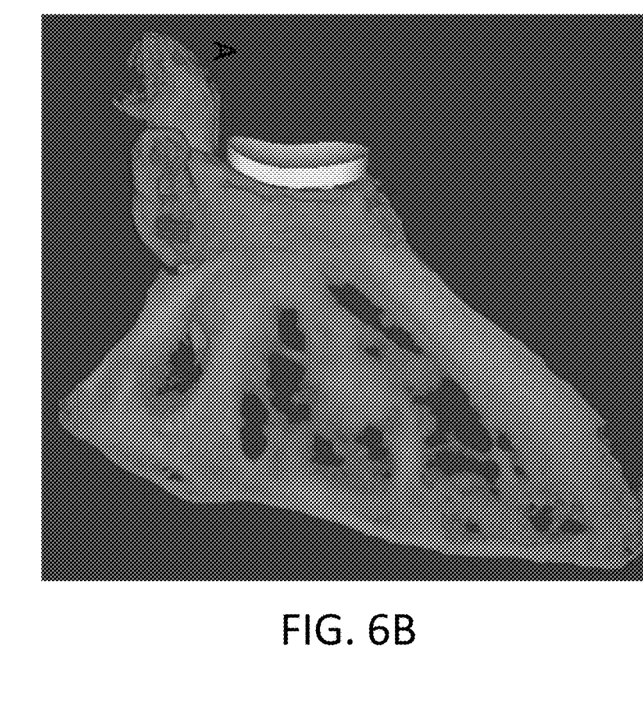

In illustrative embodiments, in conjunction with STEP 104, a surgical reference instrument (SRI) is secured to the unaltered anatomy (US) that is digitized (mapped) and registered to the pre-operative anatomy (FIGS. 6A and 6B). The SRI is digitized and added to the first composite dataset and/or generated image (CI-1) to yield a second composite dataset or image (CI-2) that now includes the SRI into the TS. The SRI and will serve as a fixed reference for subsequent composite images and surgical steps. (STEP 108) The surgical reference instrument may be any instrument which can be secured to tissue, for example, bone tissue, such as the coracoid, acromion or other part of the shoulder blade. The surgical reference instrument may be any type of mount, fixture, pin, rod instrument etc. configured to be secured relative to the tissue. The surgical reference instrument is digitized and registered within the first composite image to create the second composite image (CI-2) (3D dataset) FIGS. 6A and 6B (STEP 110) By way of example only, the digitized data of the surgical reference instrument may be obtained using a digitizer such as the MicroScribe® 3D Digitizer or other method of defining the surgical anatomy like a laser or ultrasound scanner or cameras using the principles of stereophotogrammetry to create a digitized 3D dataset. In other illustrate embodiments, any imaging technique that creates a 3D dataset from an object of interest can be used. In one illustrative embodiment, STEPS 106 and 110 may be combined into one process step.

With continued reference to the flow chart of FIG. 1, in STEP 112, the shoulder implant, is removed via one or more conventional surgical processes. In general, removal of the implant results in removal of tissue and bone structure adjacent to and leading to removal of the implant within the anatomy of a surgical field thereby defining an altered surgical field region.

In STEP 114, the surgical field, including the SRI (bone mount), after removal of the implant, i.e., the altered surgical field region is again digitized (mapped) through conventional modalities. In STEP 116, the new and altered 3D anatomy and the SRI is registered with the second composite dataset (image) (CI-2) to yield the third composite image (CI-3) (FIGS. 7A-7C) that contain the 3D digitized dataset of the altered surgical field region AS with the unaltered anatomy and SRI with the unaltered anatomy and not visualized within the surgical field but captured in the pre-operative imaging (3D dataset) to yield the TS. The altered surgical field is combined with the unaltered surgical field to define the relationship of the altered and unaltered structures to one another. This is the new surgical field to be reconstructed as the third composite image (CI-3)

This third composite image (CI-3) is used for the intraoperative surgical reconstruction of the altered surgical site in relation to landmarks from the 3D preoperative dataset (image) not altered by the surgical procedure. In this example, these landmarks, used to plan and execute the surgery after removal of the implant, are not seen in the surgical field but only seen on third composite image (CI-3) (FIGS. 9A-9E). The dataset associated with the surgical reference instrument (SRI) or bone mount integrated into the second and third composite image is utilized to guide the surgeon in performing the orthopedic procedure. (STEP 118) FIGS. 9A-9E illustrate use of the third composite image in implanting an orthopedic guide pin "p" and securement of screws "s" within columns along respective guide lines identified in association with the methodology. More specifically, the surgical reference instrument (SRI) incorporated into the second and third composite image is used as a tool to assist the surgeon in navigating the surgical procedure based upon both the altered anatomy and the unaltered anatomy. This assistance by the SRI can occur through existing computer navigation or use of adjustable patient specific instrumentation (FIGS. 9A-9E).

In other illustrative embodiments, the 3D digitized dataset of the unaltered surgical field region may be devoid of data associated with the surgical reference instrument (SRI). More specifically, it is envisioned that the surgical reference instrument (SRI) need not be utilized and that various other bone structure etc. within the unaltered surgical field may be used as a reference for the subsequent steps.

This innovation can be used in any surgical procedure when a portion of a surgical field is altered and there is a need to create a composite image (3D structural dataset) with unaltered portions of the same surgical field with or without use of an SRI.

The present invention may be utilized in conjunction with other existing technologies including virtual navigation, robotics, augment reality, or any other navigation techniques to combine the altered surgical field with the unaltered surgical anatomy prior to the surgical or revision procedure to generate a composite 3D structural data that can be represented as a 3D image. For example, and without limitation, it is envisioned that the principles of the present invention may be utilized with the system and methodology disclosed in U.S. patent application Ser. No. 18/124,626, filed Mar. 22, 2023 and entitled "METHOD AND SYSTEM FOR REMOTE ROBOTIC CONTROL OF POSITIONING OF AN INSTRUMENT" and in U.S. patent application Ser. No. 63/339,042, filed May 2, 2022 and entitled "METHOD AND SYSTEM FOR REMOTE ROBOTIC CONTROL OF POSITIONING OF AN INSTRUMENT," the entire contents of each disclosure being incorporated by reference herein. In accordance with illustrative embodiments disclosed in the '626 application, a remotely located robot adjusts the instrument at a remote location to the specific configuration to replicate the spatial target in the object. Thereafter, the adjusted instrument is removed from the robot at the remote location and returned to the procedural site of the object to perform a step in the procedure. The remotely located robot is controlled by a navigation software that compares the 3D spatial location of the instrument at the site of the object to the 3D spatial target within the object. The software defines and controls the robot to implement or perform adjustments to the instrument to replicate the spatial target on the object. After the remote robot adjusts the instrument, the instrument is returned to the site of the object and used by the operator to perform the 3D manipulation (spatial target) of the object with the SRI or bone mount.

FIGS. 10A-10G illustrate the methodology of use of the system described herein in association with a bone mount "PSI" and a remote robot (FIGS. 1OF and 10G) utilized to manipulate a patient specific instrument (psi) (FIG. 10E) at a remote location.

An additional application of this invention is to use the 3D digital data from third composite image (CI-3) to create an intraoperative patient specific implant defined by the 3D data that defines by the altered anatomy (AS) after removal of the implant and its relationship to the other unaltered anatomy (OS) not seen within the surgical field yet visualized within the third composite image (CI-3). TS that includes the altered anatomy is important to define fixation of the patient specific implant. Current and future 3D printing technology can allow for creation of a patient specific implant for reconstruction of the altered anatomy during the procedure.

As noted hereinabove, it is envisioned that the process and system of the present disclosure may have other applications in the surgery including orthopedic surgery, arthroplasty, etc. and may have application in dental procedures as well. The procedure can be applied to soft tissue procedures when the altered portions of the anatomy are associated with unaltered anatomy that does not change shape or its relationship to the altered anatomy. Moreover, the principles of the present invention may be combined with conventional navigational techniques, robotic surgical procedures, augmented reality procedures. Other applications are also contemplated.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A method, comprising:
    registering a first digitized 3D dataset of an anatomical site with a preoperative image 3D dataset of the anatomical site to form a first composite image, the preoperative image 3D dataset including data representative of an existing implant and data representative of tissue surrounding the implant;
    positioning a surgical reference relative to the anatomical site;
    obtaining a second digitized 3D dataset of the anatomical site representative of at least the surgical reference;
    registering the second digitized 3D dataset with the first composite image of the anatomical site to form a second composite image;
    removing the implant from the anatomical site and mapping the anatomical site with the removed implant to provide a mapped anatomical site;
    registering the mapped anatomical site with the second composite image thereby combining the anatomical site of the removed implant with the preoperative image 3D dataset resulting in a third digitized 3D dataset of the anatomical site of the removed implant and the surgical reference; and
    performing, with a surgical instrument, one or more surgical procedures within the anatomical site using the third digitized 3D dataset to assist in navigating the surgical instrument about the anatomical site navigation.

2. The method according to claim 1 including performing, with the surgical instrument, an orthopedic procedure.

3. The method according to claim 2 wherein the surgical instrument includes an orthopedic screw, an orthopedic pin or an orthopedic implant.

4. The method according to claim 1 including obtaining the preoperative image 3D dataset through one or more image scanning processes.

5. The method according to claim 4 wherein positioning the surgical reference relative to the anatomical site includes mounting the surgical reference to tissue within the anatomical site.

6. The method according to claim 5 wherein the surgical reference includes one of a mount, fixture, pin, rod instrument etc. configured to be secured relative to the tissue.

7. The method according to claim 1 wherein performing one or more surgical procedures includes utilizing a computer-controlled robot, the surgical instrument being coupled to the computer-controlled robot;
    wherein the computer-controlled robot utilizes the third digitized 3D dataset to manipulate the surgical instrument.

8. The method according to claim 1 wherein one or more of the steps are performed by a processor coupled to memory.

9. The method according to claim 1 wherein the preoperative image 3D dataset includes data representative of a portion of the anatomical site which is unaltered after removal of the implant, and wherein registering the mapped anatomical site with the second composite image combines the anatomical site of the removed implant with the preoperative 3D image dataset including data representative of a portion of the anatomical site which is unaltered.

10. A method, comprising:
    registering a first digitized 3D dataset of an anatomical site with a preoperative image 3D dataset of the anatomical site to form a first composite image, the preoperative image 3D dataset including data representative of an implant and data representative of tissue surrounding the implant;
    positioning a surgical reference relative to the anatomical site;
    obtaining a second digitized 3D dataset of the anatomical site representative of at least the surgical reference;
    registering the second digitized 3D dataset with the first composite image of the anatomical site to form a second composite image;
    removing the implant from the anatomical site to form an altered portion of the anatomical site;

obtaining a third digitized 3D dataset of the anatomical site representative of at least the altered portion thereof and the surgical reference;

combining the third digitized 3D dataset with the second composite image of the anatomical site to form a third composite image, the third composite image including data representative of the altered portion after removal of the implant, data representative of the preoperative image 3D dataset before removal of the implant and data representative of the surgical reference; and performing, with a surgical instrument, one or more surgical procedures within the anatomical site using the third composite image to assist in navigation of the surgical instrument about the anatomical site.

11. The method according to claim 10 including obtaining the preoperative image 3D dataset through one or more image scanning processes.

12. The method according to claim 10 wherein positioning the surgical reference relative to the anatomical site including mounting the surgical reference to tissue within the anatomical site.

13. The method according to claim 12 wherein the surgical reference includes one of a mount, fixture, pin, or a rod configured to be secured relative to the tissue.

14. The method according to claim 10 wherein the third composite image includes data representative of a portion of the anatomical site which is unaltered.

15. The method according to claim 10 wherein the third composite image includes data representative of a portion of the anatomical site which is unaltered and not visible in a surgical field.

16. The method according to claim 10 wherein performing one or more surgical procedures includes utilizing a computer-controlled robot, the surgical instrument being coupled to the computer-controlled robot;

wherein the computer-controlled robot utilizes the third digitized 3D dataset to manipulate the surgical instrument.

17. The method according to claim 10 wherein one or more of the steps are performed at least in part by a processor coupled to memory.

* * * * *